United States Patent
Miyama et al.

(10) Patent No.: US 6,921,832 B2
(45) Date of Patent: Jul. 26, 2005

(54) OPTICALLY ACTIVE FLUORINE-CONTAINING COMPOUNDS AND PROCESSES FOR THEIR PRODUCTION

(75) Inventors: Takuya Miyama, Yamaguchi-ken (JP); Toshio Naka, Yamaguchi-ken (JP); Takumi Kagawa, Yamaguchi-ken (JP)

(73) Assignee: Tosoh Corporation, Yamaguchi-ken (JP)

(*) Notice: Subject to any disclaimer, the term of this patent is extended or adjusted under 35 U.S.C. 154(b) by 52 days.

(21) Appl. No.: 10/720,686

(22) Filed: Nov. 25, 2003

(65) Prior Publication Data

US 2004/0147756 A1  Jul. 29, 2004

(30) Foreign Application Priority Data

Nov. 25, 2002 (JP) ........................................ 2002-340758

(51) Int. Cl.⁷ .................... C07D 301/03; C07D 301/19; C07D 303/38; C07D 303/12; C07C 19/08

(52) U.S. Cl. ...................... 549/523; 549/529; 549/548; 549/549; 549/560; 570/124

(58) Field of Search ................................ 549/523, 529, 549/548, 549, 560; 570/124

(56) References Cited

U.S. PATENT DOCUMENTS 6,110,729 A * 8/2000 Crosby et al. .............. 435/280

FOREIGN PATENT DOCUMENTS

WO    WO 97/38124 A    10/1997

OTHER PUBLICATIONS

Wipf et al. Methyl–and (Trifluoromethyl)alkene Peptide Isosteres: Synethesis and Evaluation of Their Potential as Beta–Turn Promoters and Peptide Mimetics.☐☐Journal of Organic Chemistry, 1998, vol. 63, p 6088–6089.*

Dillon et al, "Asymmetric synthesis of (+)–nemorensic acid–revision of the stereochemistry of the pyrrolizidine alkaloid nemorensine", Journal of the Chemical Society, Chemical Communications (1995), (16), 1645–6, XP009026929.

Kempf, et al, "Renin Inhibitors Based on Novel Dipeptide Analogues Incorporation of the Dehydrohydroxyethylene Isostere at the Scissile Bond," Journal of Medicinal Chemistry, vol. 30, No. 11, 1987, pp. 1978–1983, XP002273225.

* cited by examiner

*Primary Examiner*—Johann Richter
*Assistant Examiner*—Sikarl A. Witherspoon
(74) *Attorney, Agent, or Firm*—Nixon & Vanderhye P.C.

(57) ABSTRACT

Optically active fluorine-containing compounds of the formula (1):

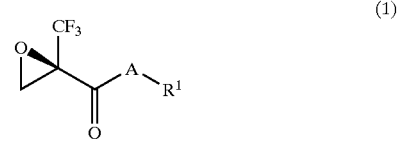

(1)

or of formula (2):

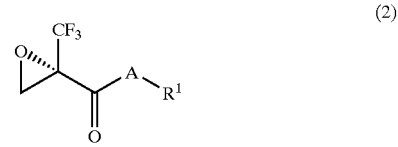

(2)

are used for producing optically active 3,3,3-trfluoro-2-hydroxy-2-methylpropionic acids.

16 Claims, No Drawings

OPTICALLY ACTIVE FLUORINE-CONTAINING COMPOUNDS AND PROCESSES FOR THEIR PRODUCTION

The present invention relates to optically active fluorine-containing novel compounds, processes for their production, and processes for producing optically active 3,3,3-trifluoro-2-hydroxy-2-methylpropionic acids, employing them.

The optically active fluorine-containing compounds of the present invention are compounds useful as intermediates for pharmaceuticals or agricultural chemicals. For example, an optically active benzyl ester of 2,3-epoxy-α,α,α,-trifluoropropionic acid as one of such compounds, can readily be led to optically active 3,3,3-trifluoro-2-hydroxy-2-methylpropionic acid which is known as a compound very useful as an intermediate for pharmaceuticals or agricultural chemical.

As a process for producing optically active 3,3,3-trifluoro-2-hydroxy-2-methylpropionic acid, a production method by optical resolution of racemic 3,3,3-trifluoro-2-hydroxy-2-methylpropionic acid by means of e.g. optically active α-phenylethylamine, has, for example, been known (e.g. JP-A-5-286915, J. Chem. Soc., 2329–2332, 1951, or J. Med. Chem., 39, 4592–4601, 1996).

Further, a process is known wherein racemic 3,3,3-trifluoro-2-hydroxy-2-methylpropionic acid ester derivative is hydrolyzed by means of lipase to produce optically active 3,3,3-trifluoro-2-hydroxy-2-methylpropionic acid (e.g. WO97/38124).

However, the production process employing an optical resolution agent, has a problem in the efficiency, since it is necessary to repeat recrystallization at least few times, and it is required to carry out a treatment to remove the optical resolution agent.

Further, in the process employing lipase, it is not possible to racemize the unnecessary optical antipode and to reuse it as a starting material, at the time of producing 3,3,3-trifluoro-2-hydroxy-2-methylpropionic acid. Thus, such a process can not be regarded as an advantageous process.

Further, no process has been known in which optically active 3,3,3-trifluoro-2-hydroxy-2-methylpropionic acid is produced efficiently by an asymmetric synthesis.

The present inventors have conducted an extensive study on a process for producing optically active 3,3,3-trifluoro-2-hydroxy-2-methylpropionic acid to solve the above-mentioned problems and as a result, have found that an optically active benzyl ester of 2,3-epoxy-α,α,α,-trifluoropropionic acid can be led to a novel optically active 2,3-epoxy-α,α,α,-trifluoropropionic acid by a hydrogenation reaction, and further that by reacting such a compound with a metal hydride, optically active 3,3,3-trifluoro-2-hydroxy-2-methylpropionic acid can be produced easily and efficiently. Further, they have been found that novel optically active fluorine-containing compounds including the optically active benzyl ester of 2,3-epoxy-α,α,α,-trifluoropropionic acid, can be obtained by asymmetrically epoxidizing specific α,α,α,-trifluoromethacrylic acid derivatives. The present invention has been accomplished on the basis of these discoveries.

Namely, the present invention provides:

1. An optically active fluorine-containing compound represented by the following formula (1):

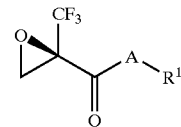

(1)

wherein A is an oxygen atom, a sulfur atom or an NH group, and $R^1$ is a methyl group, an ethyl group, a $C_{3-10}$ linear, branched or cyclic alkyl group, a $C_{6-20}$ aromatic group, a $C_{6-20}$ aromatic group having hydrogen on the aromatic ring optionally substituted by a halogen atom, a $C_{6-20}$ aromatic group having hydrogen on the aromatic ring optionally substituted by a methyl group, a $C_{6-20}$ aromatic group having hydrogen on the aromatic ring optionally substituted by an ethyl group, a $C_{6-20}$ aromatic group having hydrogen on the aromatic ring optionally substituted by a $C_{3-6}$ linear, branched or cyclic alkyl group, a $C_{6-20}$ aromatic group having hydrogen on the aromatic ring optionally substituted by a methoxy group, a $C_{6-20}$ aromatic group having hydrogen on the aromatic ring optionally substituted by an ethoxy group, a $C_{6-20}$ aromatic group having hydrogen on the aromatic ring optionally substituted by a $C_{3-6}$ linear, branched or cyclic alkyloxy group, a $C_{5-19}$ heteroaromatic group, a $C_{5-19}$ heteroaromatic group having hydrogen on the aromatic ring optionally substituted by a halogen atom, a $C_{5-19}$ heteroaromatic group having hydrogen on the aromatic ring optionally substituted by a methyl group, a $C_{5-19}$ heteroaromatic group having hydrogen on the aromatic ring optionally substituted by an ethyl group, a $C_{5-19}$ heteroaromatic group having hydrogen on the aromatic ring optionally substituted by a $C_{3-6}$ linear, branched or cyclic alkyl group, a $C_{5-19}$ heteroaromatic group having hydrogen on the aromatic ring optionally substituted by a methoxy group, a $C_{5-19}$ heteroaromatic group having hydrogen on the aromatic ring optionally substituted by an ethoxy group, a $C_{5-19}$ heteroaromatic group having hydrogen on the aromatic ring optionally substituted by a $C_{3-6}$ linear, branched or cyclic alkyloxy group, a benzyl group, a benzyl group having hydrogen on the aromatic ring optionally substituted by a halogen atom, a benzyl group having hydrogen on the aromatic ring optionally substituted by a methyl group, a benzyl group having hydrogen on the aromatic ring optionally substituted by an ethyl group, a benzyl group having hydrogen on the aromatic ring optionally substituted by a $C_{3-6}$ linear, branched or cyclic alkyl group, a 2-phenylethyl group, or a $C_{3-10}$ linear, branched or cyclic alkyl group having a $C_{6-20}$ aromatic group bonded thereto, or by the following formula (2):

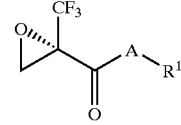

(2)

wherein A and $R^1$ are as defined above.

2. An optically active fluorine-containing compound represented by the following formula (3) or (4):

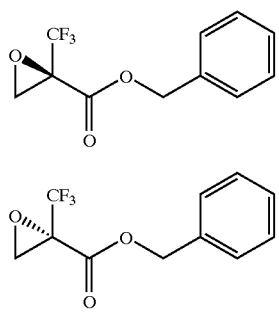

(3)

(4)

3. A process for producing an optically active fluorine-containing compound represented by the above formula (1) or (2), which comprises asymmetrically epoxidizing an α,α,α,-trifluoromethacrylic acid derivative represented by the following formula (5):

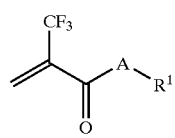

(5)

wherein A is an oxygen atom, a sulfur atom or an NH group, and $R^1$ is a methyl group, an ethyl group, a $C_{3-10}$ linear, branched or cyclic alkyl group, a $C_{6-20}$ aromatic group, a $C_{6-20}$ aromatic group having hydrogen on the aromatic ring optionally substituted by a halogen atom, a $C_{6-20}$ aromatic group having hydrogen on the aromatic ring optionally substituted by a methyl group, a $C_{6-20}$ aromatic group having hydrogen on the aromatic ring optionally substituted by an ethyl group, a $C_{6-20}$ aromatic group having hydrogen on the aromatic ring optionally substituted by a $C_{3-6}$ linear, branched or cyclic alkyl group, a $C_{6-20}$ aromatic group having hydrogen on the aromatic ring optionally substituted by a methoxy group, a $C_{6-20}$ aromatic group having hydrogen on the aromatic ring optionally substituted by an ethoxy group, a $C_{6-20}$ aromatic group having hydrogen on the aromatic ring optionally substituted by a $C_{3-6}$ linear, branched or cyclic alkyloxy group, a $C_{5-19}$ heteroaromatic group, a $C_{5-19}$ heteroaromatic group having hydrogen on the aromatic ring optionally substituted by a halogen atom, a $C_{5-19}$ heteroaromatic group having hydrogen on the aromatic ring optionally substituted by a methyl group, a $C_{5-19}$ heteroaromatic group having hydrogen on the aromatic ring optionally substituted by an ethyl group, a $C_{5-19}$ heteroaromatic group having hydrogen on the aromatic ring optionally substituted by a $C_{3-6}$ linear, branched or cyclic alkyl group, a $C_{5-19}$ heteroaromatic group having hydrogen on the aromatic ring optionally substituted by a methoxy group, a $C_{5-19}$ heteroaromatic group having hydrogen on the aromatic ring optionally substituted by an ethoxy group, a $C_{5-19}$ heteroaromatic group having hydrogen on the aromatic ring optionally substituted by a $C_{3-6}$ linear, branched or cyclic alkyloxy group, a benzyl group, a benzyl group having hydrogen on the aromatic ring optionally substituted by a halogen atom, a benzyl group having hydrogen on the aromatic ring optionally substituted by a methyl group, a benzyl group having hydrogen on the aromatic ring optionally substituted by an ethyl group, a benzyl group having hydrogen on the aromatic ring optionally substituted by a $C_{3-6}$ linear, branched or cyclic alkyl group, a 2-phenylethyl group, or a $C_{3-10}$ linear, branched or cyclic alkyl group having a $C_{6-20}$ aromatic group bonded thereto.

4. The process for producing an optically active fluorine-containing compound represented by the above formula (1) or (2), wherein the α,α,α,-trifluoromethacrylic acid derivative represented by the formula (5) is subjected to the asymmetric epoxidizing reaction in the presence of a catalyst comprising (A) a rare earth metal alkoxide, (B) optically active 1,1'-bi-2-naphthol, (C) triphenylphosphine oxide and (D) cumene hydroperoxide or tert-butyl hydroperoxide.

5. An optically active fluorine-containing compound represented by the following formula (6) or (7):

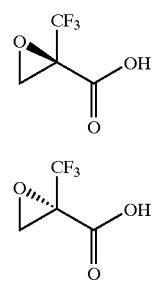

(6)

(7)

6. A process for producing the optically active fluorine-containing compound represented by the above formula (6), which comprises hydrolyzing or hydrogenating the optically active fluorine-containing compound represented by the above formula (3).

7. A process for producing the optically active fluorine-containing compound represented by the above formula (7), which comprises hydrolyzing or hydrogenating an optically active fluorine-containing compound represented by the above formula (4).

8. A process for producing (R)-3,3,3-trifluoro-2-hydroxy-2-methylpropionic acid, which comprises reacting the optically active fluorine-containing compound represented by the above formula (6), with a metal hydride.

9. A process for producing (S)-3,3,3-trifluoro-2-hydroxy-2-methylpropionic acid, which comprises reacting the optically active fluorine-containing compound represented by the above formula (7), with a metal hydride.

Now, the present invention will be described in detail.

The optically active fluorine-containing compound represented by the above formula (1) or (2) of the present invention, can be produced by asymmetrically epoxidizing the α,α,α, -trifluoromethacrylic acid derivative represented by the above formula (5).

In the present invention, in the above formula (1), (2) or (5), A represents an oxygen atom, a sulfur atom or an NH group. Among them, an oxygen atom is preferred as A.

Further, in the present invention, in the above formula (1), (2) or (5), $R^1$ is a methyl group, an ethyl group, a $C_{3-10}$ linear, branched or cyclic alkyl group, a $C_{6-20}$ aromatic group, a $C_{6-20}$ aromatic group having hydrogen on the aromatic ring optionally substituted by a halogen atom, a $C_{6-20}$ aromatic group having hydrogen on the aromatic ring optionally substituted by a methyl group, a $C_{6-20}$ aromatic group having hydrogen on the aromatic ring optionally substituted by an ethyl group, a $C_{6-20}$ aromatic group having hydrogen on the aromatic ring optionally substituted by a $C_{3-6}$ linear, branched or cyclic alkyl group, a $C_{6-20}$ aromatic group having hydrogen on the aromatic ring optionally substituted by a methoxy group, a $C_{6-20}$ aromatic group having hydrogen on the aromatic ring optionally substituted by an ethoxy group, a $C_{6-20}$ aromatic group having hydrogen on the aromatic ring optionally substituted by a $C_{3-6}$ linear, branched or cyclic alkyloxy group, a $C_{5-19}$ heteroaromatic group, a $C_{5-19}$ heteroaromatic group having hydrogen on the aromatic ring optionally substituted by a halogen atom, a $C_{5-19}$ heteroaromatic group having hydrogen on the aromatic ring optionally substituted by a methyl group, a $C_{5-19}$ heteroaromatic group having hydrogen on the aromatic ring optionally substituted by an ethyl group, a $C_{5-19}$ heteroaromatic group having hydrogen on the aromatic ring optionally substituted by a $C_{3-6}$ linear, branched or cyclic alkyl group, a $C_{5-19}$ heteroaromatic group having hydrogen on the aromatic ring optionally substituted by a methoxy group, a $C_{5-19}$ heteroaromatic group having hydrogen on the aromatic ring optionally substituted by an ethoxy group, a $C_{5-19}$ heteroaromatic group having hydrogen on the aromatic ring optionally substituted by a $C_{3-6}$ linear, branched or cyclic alkyloxy group, a benzyl group, a benzyl group having hydrogen on the aromatic ring optionally substituted by a halogen atom, a benzyl group having hydrogen on the aromatic ring optionally substituted by a methyl group, a benzyl group having hydrogen on the aromatic ring optionally substituted by an ethyl group, a benzyl group having hydrogen on the aromatic ring optionally substituted by a $C_{3-6}$ linear, branched or cyclic alkyl group, a 2-phenylethyl group, or a $C_{3-10}$ linear, branched or cyclic alkyl group having a $C_{6-20}$ aromatic group bonded thereto. Among them, $R^1$ is preferably a tert-butyl group, a phenyl group, a phenyl group having hydrogen on the aromatic ring substituted by a halogen atom, or a benzyl group, particularly preferably a benzyl group.

The compound represented by the above formula (1) or (2) of the present invention is not particularly limited, but specifically, the compound wherein A is an oxygen atom, and $R^1$ is a $C_{1-10}$ alkyl group may, for example, be (R)-2,3-epoxy-2-(trifluoromethyl)propionic acid methyl ester, (R)-2,3-epoxy-2-(trifluoromethyl)propionic acid ethyl ester, (R)-2,3-epoxy-2-(trifluoromethyl)propionic acid isopropyl ester, (R)-2,3-epoxy-2-(trifluoromethyl)propionic acid n-butyl ester, (R)-2,3-epoxy-2-(trifluoromethyl)propionic acid n-butyl ester, (R)-2,3-epoxy-2-(trifluoromethyl)propionic acid tert-butyl ester, (R)-2,3-epoxy-2-(trifluoromethyl)propionic acid cyclohexyl ester, (R)-2,3-epoxy-2-(trifluoromethyl)propionic acid cyclohexylmethyl ester or (R)-2,3-epoxy-2-(trifluoromethyl)propionic acid 2-cyclohexylethyl ester.

Further, the compound represented by the above formula (1) or (2) wherein A is an oxygen atom, and $R^1$ is a $C_{6-20}$ aromatic group, may, for example, be (R)-2,3-epoxy-2-(trifluoromethyl)propionic acid phenyl ester, (R)-2,3-epoxy-2-(trifluoromethyl)propionic acid p-chlorophenyl ester, (R)-2,3-epoxy-2-(trifluoromethyl)propionic acid m-chlorophenyl ester, (R)-2,3-epoxy-2-(trifluoromethyl)propionic acid o-chlorophenyl ester, (R)-2,3-epoxy-2-(trifluoromethyl)propionic acid p-bromophenyl ester, (R)-2,3-epoxy-2-(trifluoromethyl)propionic acid m-bromophenyl ester, (R)-2,3-epoxy-2-(trifluoromethyl)propionic acid o-bromophenyl ester, (R)-2,3-epoxy-2-(trifluoromethyl)propionic acid p-fluorophenyl ester, (R)-2,3-epoxy-2-(trifluoromethyl)propionic acid m-fluorophenyl ester, (R)-2,3-epoxy-2-(trifluoromethyl)propionic acid o-fluorophenyl ester, (R)-2,3-epoxy-2-(trifluoromethyl)propionic acid p-methoxyphenyl ester, (R)-2,3-epoxy-2-(trifluoromethyl)propionic acid m-methoxyphenyl ester or (R)-2,3-epoxy-2-(trifluoromethyl)propionic acid o-methoxyphenyl ester.

Further, the compound represented by the above formula (1) or (2) wherein A is an oxygen atom, and $R^1$ is a $C_{1-10}$ alkyl group having a $C_{6-20}$ aromatic group bonded thereto, may, for example, be (R)-2,3-epoxy-2-(trifluoromethyl) propionic acid benzyl ester, (R)-2,3-epoxy-2-(trifluoromethyl)propionic acid 2-phenylethyl ester, (R)-2,3-epoxy-2-(trifluoromethyl)propionic acid (p-chlorophenyl) methyl ester, (R)-2,3-epoxy-2-(trifluoromethyl)propionic acid (p-bromophenyl)methyl ester or (R)-2,3-epoxy-2-(trifluoromethyl)propionic acid (p-fluorophenyl)methyl ester.

Further, the compound represented by the above formula (1) or (2) wherein A is an NH group and $R^1$ is a $C_{1-10}$ alkyl group, may, for example, be (R)-2,3-epoxy-2-(trifluoromethyl)propionic acid methylamide, (R)-2,3-epoxy-2-(trifluoromethyl)propionic acid ethylamide, (R)-2,3-epoxy-2-(trifluoromethyl)propionic acid isopropylamide, (R)-2,3-epoxy-2-(trifluoromethyl)propionic acid n-butylamide, (R)-2,3-epoxy-2-(trifluoromethyl)propionic acid n-butylamide, (R)-2,3-epoxy-2-(trifluoromethyl) propionic acid tert-butylamide, (R)-2,3-epoxy-2-(trifluoromethyl)propionic acid cyclohexylamide, (R)-2,3-epoxy-2-(trifluoromethyl)propionic acid cyclohexylmethylamide or (R)-2,3-epoxy-2-(trifluoromethyl)propionic acid 2-cyclohexylethylamide.

Further, the compound represented by the above formula (1) or (2) wherein A is an NH group and $R^1$ is a $C_{6-20}$ aromatic group, may, for example, be (R)-2,3-epoxy-2-(trifluoromethyl)propionic acid anilide, (R)-2,3-epoxy-2-(trifluoromethyl)propionic acid p-chlorophenylamide, (R)-2,3-epoxy-2-(trifluoromethyl)propionic acid m-chlorophenylamide, (R)-2,3-epoxy-2-(trifluoromethyl) propionic acid o-chlorophenylamide, (R)-2,3-epoxy-2-(trifluoromethyl)propionic acid, p-bromophenylamide, (R)-2,3-epoxy-2-(trifluoromethyl)propionic acid m-bromophenylamide, (R)-2,3-epoxy-2-(trifluoromethyl) propionic acid o-bromophenylamide, (R)-2,3-epoxy-2-(trifluoromethyl)propionic acid p-fluorophenylamide, (R)-2,3-epoxy-2-(trifluoromethyl)propionic acid m-fluorophenylamide, (R)-2,3-epoxy-2-(trifluoromethyl) propionic acid o-fluorophenylamide, (R)-2,3-epoxy-2-(trifluoromethyl)propionic acid p-methoxyphenylamide, (R)-2,3-epoxy-2-(trifluoromethyl)propionic acid m-methoxyphenylamide or (R)-2,3-epoxy-2-(trifluoromethyl)propionic acid o-methoxyphenylamide.

Further, the compound represented by the above formula (1) or (2) wherein A is an NH group, and $R^1$ is a $C_{1-10}$ alkyl group having a $C_{6-20}$ aromatic group bonded thereto, may, for example, be (R)-2,3-epoxy-2-(trifluoromethyl)propionic acid benzylamide, (R)-2,3-epoxy-2-(trifluoromethyl) propionic acid 2-phenylethylamide, (R)-2,3-epoxy-2-(trifluoromethyl)propionic acid (p-chlorophenyl) methylamide, (R)-2,3-epoxy-2-(trifluoromethyl)propionic acid (p-bromophenyl)methylamide or (R)-2,3-epoxy-2-(trifluoromethyl)propionic acid (p-fluorophenyl) methylamide.

The compound represented by the above formula (1) or (2) of the present invention includes not only the above-mentioned such (R) isomers, but also (S) isomers which are antipodes of the (R) isomers. In the present invention, it is possible to produce the optically active fluorine-containing compound represented by the above formula (1) or (2) by asymmetrically epoxidizing an α,α,α-trifluoromethacrylic acid derivative represented by the above formula (5).

The compound represented by the above formula (5) of the present invention is not particularly limited, but specifically, the compound wherein A is an oxygen atom, and $R^1$ is a $C_{1-10}$ alkyl group, may, for example, be α,α,α-trifluoromethacrylic acid methyl ester, α,α,α- trifluoromethacrylic acid ethyl ester, α,α,α-trifluoromethacrylic acid isopropyl ester, α,α,α-trifluoromethacrylic acid n-butyl ester, α,α,α-trifluoromethacrylic acid n-butyl ester, α,α,α-trifluoromethacrylic acid tert-butyl ester, α,α,α-trifluoromethacrylic acid cyclohexyl ester, α,α,α-trifluoromethacrylic acid cyclohexylmethyl ester or α,α,α-trifluoromethacrylic acid 2-cyclohexylethyl ester.

Further, the compound represented by the above formula (5) wherein A is an oxygen atom, and $R^1$ is a $C_{6-20}$ aromatic group, may, for example, be α,α,α-trifluoromethacrylic acid phenyl ester, α,α,α-trifluoromethacrylic acid p-chlorophenyl ester, α,α,α-trifluoromethacrylic acid m-chlorophenyl ester, α,α,α-trifluoromethacrylic acid o-chlorophenyl ester, α,α,α-trifluoromethacrylic acid p-bromophenyl ester, α,α,α-trifluoromethacrylic acid m-bromophenyl ester, α,α,α-trifluoromethacrylic acid o-bromophenyl ester, α,α,α-trifluoromethacrylic acid p-fluorophenyl ester, α,α,α-trifluoromethacrylic acid m-fluorophenyl ester, α,α,α-trifluoromethacrylic acid o-fluorophenyl ester, α,α,α-trifluoromethacrylic acid p-methoxyphenyl ester, α,α,α-trifluoromethacrylic acid m-methoxyphenyl ester or α,α,α-trifluoromethacrylic acid o-methoxyphenyl ester.

Further, the compound represented by the above formula (5) wherein A is an oxygen atom, and $R^1$ is a $C_{1-10}$ alkyl group having a $C_{6-20}$ aromatic group bonded thereto, may, for example, be α,α,α-trifluoromethacrylic acid benzyl ester, α,α,α-trifluoromethacrylic acid 2-phenylethyl ester, α,α,α-trifluoromethacrylic acid (p-chlorophenyl)methyl ester, α,α,α-trifluoromethacrylic acid (p-bromophenyl) methyl ester or α,α,α-trifluoromethacrylic acid (p-fluorophenyl)methyl ester.

Further, the compound represented by the above formula (5) wherein A is an NH group, and $R^1$ is a $C_{1-10}$ alkyl group, may, for example, be α,α,α-trifluoromethacrylic acid methylamide, α,α,α-trifluoromethacrylic acid ethylamide, α,α,α-trifluoromethacrylic acid isopropylamide, α,α,α-trifluoromethacrylic acid n-butylamide, α,α,α-trifluoromethacrylic acid n-butylamide, α,α,α-trifluoromethacrylic acid tert-butylamide, α,α,α-trifluoromethacrylic acid cyclohexyl amide, α,α,α-trifluoromethacrylic acid cyclohexyl methylamide or α,α,α-trifluoromethacrylic acid 2-cyclohexyl ethylamide.

Further, the compound represented by the above formula (3) wherein A is an NH group, and $R^1$ is a $C_{6-20}$ aromatic group, may, for example, be α,α,α-trifluoromethacrylic acid anilide, α,α,α-trifluoromethacrylic acid p-chlorophenylamide, α,α,α-trifluoromethacrylic acid m-chlorophenylamide, α,α,α-trifluoromethacrylic acid o-chlorophenylamide, α,α,α-trifluoromethacrylic acid p-bromophenylamide, α,α,α-trifluoromethacrylic acid m-bromophenylamide, α,α,α-trifluoromethacrylic acid o-bromophenylamide, α,α,α-trifluoromethacrylic acid p-fluorophenylamide, α,α,α-trifluoromethacrylic acid m-fluorophenylamide, α,α,α-trifluoromethacrylic acid o-fluorophenylamide, α,α,α-trifluoromethacrylic acid p-methoxyphenylamide, α,α,α-trifluoromethacrylic acid m-methoxyphenylamide or α,α,α-trifluoromethacrylic acid o-methoxyphenylamide.

Further, the compound represented by the above formula (5) wherein A is an NH group, and $R^1$ is a $C_{1-10}$ alkyl group having a $C_{6-20}$ aromatic group bonded thereto, may, for example, be α,α,α-trifluoromethacrylic acid benzylamide, α,α,α,-trifluoromethacrylic acid 2-phenylethylamide, α,α,α-trifluoromethacrylic acid (p-chlorophenyl)methylamide, α,α,α-trifluoromethacrylic acid (p-bromophenyl) methylamide or α,α,α-trifluoromethacrylic acid (p-fluorophenyl)methylamide.

In the process of the present invention, a method for preparing the α,α,α-trifluoromethacrylic acid derivative represented by the above formula (5) is not particularly limited. However, it may be prepared, for example, by treating α,α,α-trifluoromethacrylic acid with thionyl chloride to obtain α,α,α-trifluoromethacrylic acid chloride, which is then reacted with an alcohol represented by R1-A-H, a phenol and an amine in the presence of a base such as triethylamine in a solvent such as diethyl ether or dichloromethane.

In the process of the present invention, various asymmetric epoxidizing reactions may be used for the preparation of the optically active fluorine-containing compound represented by the above formula (1) or (2). For example, a method of employing titanium tetraisopropoxide or a tartaric acid derivative, a method of employing a quaternary ammonium salt such as a cinchona alkaloid derivative, a method of employing a metal such as zinc, lithium, magnesium or a lanthanoid, or an asymmetric ligand of e.g. an optically active 1,1'-bi-2-naphthol derivative, a method of employing an optically active dioxirane, or a method of employing a salen-manganese complex, may, for example, be mentioned. However, in the process of the present invention, it is preferred to carry out the asymmetric epoxidizing reaction in the presence of a catalyst comprising (A) a rare earth metal alkoxide, (B) optically active 1,1'-bi-2-naphthol, (C) triphenylphosphine oxide, and (D) cumene hydroperoxide or tert-butyl hydroperoxide.

In the process of the present invention, (A) the rare earth metal alkoxide to be used for the asymmetric epoxidizing reaction, is not particularly limited. However, specifically, it may, for example, be scandium trimethoxide, scandium triethoxide, scandium triisopropoxide, scandium tri-n-propoxide, yttrium trimethoxide, yttrium triethoxide, yttrium triisopropoxide, yttrium tri-n-propoxide, lanthanum trimethoxide, lanthanum triethoxide, lanthanum triisopropoxide, lanthanum tri-n-propoxide, cerium trimethoxide, cerium triethoxide, cerium triisopropoxide, cerium tri-n-propoxide, praseodymium trimethoxide, praseodymium triethoxide, praseodymium triisopropoxide, praseodymium tri-n-propoxide, neodymium trimethoxide, neodymium triethoxide, neodymium triisopropoxide, neodymium tri-n-propoxide, samarium trimethoxide, samarium triethoxide, samarium triisopropoxide, samarium tri-n-propoxide, europium trimethoxide, europium triethoxide, europium triisopropoxide, europium tri-n-propoxide, gadolinium trimethoxide, gadolinium triethoxide, gadolinium triisopropoxide, gadolinium tri-n-propoxide, terbium trimethoxide, terbium triethoxide, terbium triisopropoxide, terbium tri-n-propoxide, dysprosium trimethoxide, dysprosium triethoxide, dysprosium triisopropoxide, dysprosium tri-n-propoxide, holmium trimethoxide, holmium triethoxide, holmium triisopropoxide, holmium tri-n-propoxide, erbium trimethoxide, erbium triethoxide, erbium triisopropoxide, erbium tri-n-propoxide, thulium trimethoxide, thulium triethoxide, thulium triisopropoxide, thulium tri-n-propoxide, ytterbium trimethoxide, ytterbium triethoxide, ytterbium triisopropoxide, ytterbium tri-n-propoxide, ruthenium trimethoxide, ruthenium triethoxide, ruthenium triisopropoxide or ruthenium tri-n-propoxide.

In the process of the present invention, (A) the rare earth metal alkoxide is preferably a lanthanoid triisopropoxide such as lanthanum triisopropoxide, cerium triisopropoxide, praseodymium triisopropoxide, neodymium triisopropoxide, samarium triisopropoxide, europium triisopropoxide, gadolinium triisopropoxide, terbium triisopropoxide, dysprosium triisopropoxide, holmium triisopropoxide, erbium triisopropoxide, thulium triisopropoxide, ytterbium triisopropoxide or ruthenium triisopropoxide. Among them, lanthanum triisopropoxide or ytterbium triisopropoxide is further preferred, and lanthanum triisopropoxide is particularly preferred.

In the process of the present invention, method of preparing the rare earth metal alkoxide is not particularly limited. Further, with respect to the amount of the rare earth metal alkoxide, it is used usually in an amount of from 0.1 mol % to 30 mol % to the $\alpha,\alpha,\alpha$-trifluoromethacrylic acid benzyl ester to be used in the present invention.

In the process of the present invention, the amount of the optically active 1,1'-bi-2-naphthol to be used for the asymmetric epoxidizing reaction is usually from 1 to 2 times by mol, preferably from 1 to 1.2 times by mol, to the lanthanoid triisopropoxide to be used for the reaction.

In the process of the present invention, the amount of the triphenylphosphine oxide to be used for the asymmetric epoxidizing reaction, is usually from 1 to 5 times by mol, preferably from 1.1 to 3 times by mol, to the lanthanoid triisopropoxide to be used for the reaction.

In the process of the present invention, the amount of cumene hydroperoxide or tert-butyl hydroperoxide to be used for the asymmetric epoxidizing reaction is usually from 1 to 4 times by mol to the lanthanoid triisopropoxide at the time of forming the catalyst, and further, at the time of the reaction, it is used usually in an amount of from 1 to 2 times by mol to the $\alpha,\alpha,\alpha$,-trifluoromethacrylic acid benzyl ester to be used for the reaction.

In the process of the present invention, for the preparation of the optically active fluorine-containing compound represented by the above formula (1), it is particularly preferred to carry out the asymmetric epoxidizing reaction by cumene hydroperoxide by means of a catalyst comprising (A) a lanthanoid triisopropoxide as the rare earth metal alkoxide, (B) (R)-1,1'-bi-2-naphthol as the optically active 1,1'-bi-2-naphthol, (C) triphenylphosphine oxide and (D) cumene hydroperoxide. Likewise, for the preparation of the optically active fluorine-containing compound represented by the above formula (2), it is particularly preferred to carry out the asymmetric epoxidizing reaction by cumene hydroperoxide by means of a catalyst comprising (A) a lanthanoid triisopropoxide as the rare earth metal alkoxide, (B) (S)-1,1'-bi-2-naphthol as the optically active 1,1'-bi-2-naphthol, (C) triphenylphosphine oxide and (D) cumene hydroperoxide.

In the process of the present invention, at the time of the asymmetric epoxidizing reaction, a catalyst solution comprising (A) a rare earth metal alkoxide, (B) an optically active 1,1'-bi-2-naphthol, (C) triphenylphosphine oxide and (D) cumene hydroperoxide or tert-butyl hydroperoxide, may preliminarily be prepared, and the substrate and cumene hydroperoxide or tert-butyl hydroperoxide are mixed and supplied to the catalyst solution, to carry out the reaction. Otherwise, the substrate and cumene hydroperoxide or tert-butyl hydroperoxide may respectively separately supplied to the catalyst solution to carry out the reaction.

In the process of the present invention, at the time of the asymmetric epoxidizing reaction, in order to maintain the reaction system to be anhydrous, a zeolite such as powdery or molded molecular sieves 3A or molecular sieves 4A may be used in a proper amount, as the case requires.

In the process of the present invention, the solvent useful for the asymmetrical epoxidizing reaction is not particularly limited. However, specifically, it may, for example, be an ether such as tetrahydrofuran (hereinafter referred to simply as THF), diethyl ether or diisopropyl ether, or an aromatic hydrocarbon such as benzene, toluene or ethylbenzene. Preferred is an ether, and particularly preferred is THF.

In the process of the present invention, with respect to the reaction temperature, the asymmetric epoxidizing reaction can be carried out within a range of from $-50°$ C. to $50°$ C. However, in order to obtain the optically active fluorine-containing compound represented by the above formula (1) or (2) in a high optical purity, it is preferably carried out at a temperature of from $-30°$ C. to $10°$ C.

In the process of the present invention, the reaction time for the asymmetric epoxidizing reaction varies depending upon the substrate concentration, the amount of the catalyst, the concentration of the catalyst and the reaction temperature and is not particularly limited, but the reaction is usually completed from 2 to 24 hours after adding the substrate.

In the process of the present invention, post-treatment after the asymmetric epoxidizing reaction is not particularly limited. Usually, after decomposing the catalyst by adding a saturated ammonium chloride aqueous solution, excess cumene hydroperoxide is decomposed by e.g. an aqueous sodium hydrogen sulfite solution, followed by purification by e.g. silica gel chromatography, whereby it is possible to obtain the is desired optically active fluorine-containing compound represented by the above formula (1) or (2) in an optical purity of from 60 to 95% ee.

The optically active fluorine-containing compound represented by the above formula (6) of the present invention can be produced by hydrolyzing the (2R)-2,3-epoxy-2-(trifluoromethyl)propionic acid derivative represented by the above formula (1). Likewise, the optically active fluorine-containing compound represented by the above formula (7) can be produced by hydrolyzing the (2R)-2,3-epoxy-2-(trifluoromethyl)propionic acid derivative represented by the above formula (2).

The conditions for the hydrolysis of the present invention are not particularly limited. However, at the time of hydrolysis of the ester, an alkali metal hydroxide such as lithium hydroxide, sodium hydroxide or potassium hydroxide is used in an amount of from 1.2 to 3 times by mol to the optically active 2,3-epoxy-2-(trifluoromethyl)propionic acid derivative to be reacted, and the reaction is carried out in a mixed solvent of water and methanol within a temperature range of from 0 to $60°$ C. for from 1 to 12 hours, whereby the compound represented by the formula (6) or (7) can be obtained as the desired product. Further, with respect to the hydrolysis of the amide, the reaction is carried out in a solvent in the presence of from 10 to 100 mol % of hydrochloric acid within a temperature range of from 0 to $60°$ C. for from 1 to 12 hours to obtain the optically active fluorine-containing compound of the above formula (6) or (7) as the desired product.

The conditions for post-treatment after the hydrolysis of the present invention are not particularly limited, and the desired product is obtained by extraction with a solvent such as ethyl acetate under an acidic condition.

The optically active fluorine-containing compound represented by the above formula (6) of the present invention can be produced by hydrogenating (2R)-2,3-epoxy-2-(trifluoromethyl)propionic acid benzyl ester represented by the above formula (3) in the presence of a metal catalyst. Likewise, the optically active fluorine-containing compound represented by the above formula (7) can be produced by hydrogenating the (2S)-2,3-epoxy-2-(trifluoromethyl) propionic acid benzyl ester represented by the above formula (4) in the presence of a metal catalyst. The metal catalyst to be used for the hydrogenation reaction in the processes of the present invention is not particularly limited. However, specifically, platinum, platinum oxide, palladium, palladium hydroxide, rhodium, ruthenium, iridium or Raney nickel may, for example, be mentioned. Further, one having such a metal supported on carbon, alumina, calcium sulfate or the like may be mentioned. Preferred is platinum or platinum oxide.

The amount of the metal catalyst to be used for the hydrogenation reaction in the processes of the present invention varies depending upon the type of the catalyst and is not particularly limited. However, it is usually used in an amount of from 0.1 to 20 wt %, as calculated as the metal weight to the optically active 2,3-epoxy-2-(trifluoromethyl)propionic acid benzyl ester represented by the above formula (3) or (4).

The solvent useful for the hydrogenation reaction in the processes of the present invention, is not particularly limited so long as it is inert to the reaction. However, specifically, water, an alcohol such as methanol or ethanol, ethyl acetate, acetic acid, an ether, benzene, hexane or dioxane may, for example, be mentioned. Among them, preferred is an alcohol, and methanol is particularly preferred.

The reaction temperature and the reaction time for the hydrogenation reaction in the processes of the present invention, vary depending upon the type of the catalyst, but usually the reaction will be completed under atmospheric pressure or an elevated pressure within a range of from −20° C. to 30° C. in from 5 to 24 hours.

In the processes of the present invention, post-treatment after the hydrogenation reaction is not particularly limited. However, usually, after filtering the catalyst off, the solvent is distilled under reduced pressure to obtain the desired optically active fluorine-containing compound represented by the above formula (6) or (7).

In the processes of the present invention, the optically active 2,3-epoxy-2-(trifluoromethyl)propionic acid benzyl ester represented by the above formula (3) or (4), to be used for the hydrogenation reaction, is not necessarily highly pure and, for example, may be used in the form of a composition containing cumyl alcohol as a decomposition product of cumene hydroperoxide, an optically active 1,1'-bi-2-naphthol, triphenylphosphine oxide, etc. After completion of the asymmetric epoxidizing reaction of the α,α,α,-trifluoromethacrylic acid benzyl ester, whereby the hydrogenation reaction will proceed under the above-mentioned reaction conditions. In such a case, post-treatment is not particularly limited, but usually, the catalyst is filtered off, the solvent is distilled off under reduced pressure, and then ethyl acetate, water and sodium hydrogen carbonate are added, followed by stirring and liquid separation, whereupon the aqueous layer is acidified with e.g. hydrochloric acid and extracted with ethyl acetate, whereby the desired optically active fluorine-containing compound represented by the above formula (6) or (7) can be obtained.

By reducing the optically active fluorine-containing compound represented by the above formula (6) of the present invention with a metal hydride, it is possible to produce (R)-3,3,3-trifluoro-2-hydroxy-2-methylpropionic acid. Likewise, by reducing the optically active fluorine-containing compound represented by the above formula (7) with a metal hydride, it is possible to produce (S)-3,3,3-trifluoro-2-hydroxy-2-methylpropionic acid.

In the processes of the present invention, the metal hydride to be used for the reduction reaction is not particularly limited. However, specifically, sodium boron hydride, sodium boron trimethoxy hydride, sodium boron cyanide hydride, sodium boron triacetoxy hydride, lithium boron hydride, lithium boron tri-s-butyl hydride, lithium boron triethyl hydride, lithium boron tricyamyl hydride, potassium boron hydride, potassium boron tri-s-butyl hydride, potassium boron tricyamyl hydride, zinc boron hydride, calcium boron hydride, lithium aluminum hydride, lithium aluminum trimethoxy hydride, lithium aluminum tri-t-butoxy hydride, sodium aluminum bis(2-methoxyethoxy) hydride or aluminum diisobutyl hydride, may, for example, be mentioned. Among them, preferred is aluminum diisobutyl hydride.

In the processes of the present invention, the amount of the metal hydride to be used for the reduction reaction is usually from 1 to 5 equivalents to the optically active 2,3-epoxy-2-(trifluoromethyl)propionic acid represented by the above formula (6) or (7).

In the processes of the present invention, the solvent useful for the reduction reaction varies depending upon the type of the metal hydride and is not particularly limited so long as it is inert to the reaction. Specifically, an alcohol such as methanol or ethanol, an ether such as THF, diethyl ether or diisopropyl ether, an aliphatic hydrocarbon such as hexane or heptane, a halogenated hydrocarbon such as dichloromethane or chloroform, or an aromatic hydrocarbon such as benzene or toluene, may, for example, be mentioned. For example, in a case where aluminum diisobutyl hydride is used as the metal hydride, toluene, hexane or the like, or a halogenated hydrocarbon mixture thereof with a dichloromethane or the like, is preferred.

In the processes of the present invention, the reaction temperature and the reaction time in the reduction reaction are not particularly limited, but the reaction will usually be completed within a range of from −100° C. to 20° C. in from 1 to 24 hours.

In the processes of the present invention, post-treatment after the reduction reaction is not particularly limited, but it is common that methanol is dropwise added at −80° C. or lower to terminate the reaction, and the reaction solution is acidified with e.g. hydrochloric acid, and then sodium chloride is added and extracted with ethyl ether to obtain (R)-3,3,3-trifluoro-2-hydroxy-2-methylpropionic acid or (S)-3,3,3-trifluoro-2-hydroxy-2-methylpropionic acid. The obtained optically active 3,3,3-trifluoro-2-hydroxy-2-methylpropinic acid can be recrystallized from a solvent such as toluene to bring the optical purity usually to a level of 99.9% ee or higher.

The present invention provides novel optically active fluorine-containing compounds and thus is industrially useful.

Among the derivatives of the present invention, the optically active 2,3-epoxy-2-(trifluoromethyl)propionic acid benzyl ester represented by the above formula (3) or (4) is capable of easily and efficiently producing optically active 3,3,3-trifluoro-2-hydroxy-2-methylpropionic acid without using an optical resolution agent or enzyme, and accordingly, the production process of the present invention is a process which is simple and efficient as compared with the conventional processes and which is suitable for mass production, and thus it is industrially very useful.

Now, the present invention will be described in further detail with reference to Examples. However, it should be understood that the present invention is by no means restricted to such specific Examples. The following instruments were used for the analyses of the compounds.

¹H-NMR and ¹³C-NMR Measurements
Carried out by means of Gemini-200, manufactured by Varian.

Infrared Absorption Measurement
Carried out by means of 2000FT-IR, manufactured by Perkin Elmer.

Elemental Analysis
C, H: Carried out by means of 2400IICH, manufactured by Perkin Elmer.

F: Carried out by means of HPLC; column: TSKgel IC-Anion-PWXL PEEK (4.6 mm ID×750 mm), manufactured by Tosoh Corporation; eluent: 1.3 mM gluconic acid-borax buffer; detector: electrical conductivity tester.

Mass Analysis
Carried out by means of M-80B, manufactured by Hitachi, Ltd.

Measurement of Specific Rotation
Carried out by means of SEPA-300, manufactured by HORIBA, Ltd.

REFERENCE EXAMPLE 1

Preparation of α,α,α-trifluoromethacrylic acid benzyl ester

Into a 500 ml two-necked round-bottomed flask equipped with a condenser and a stirrer, α,α,α-trifluoromethacrylic acid (154.0 g, 1.10 mol) and thionyl chloride (170.1 g, 1.43 mol) were charged and refluxed for 5 hours. By distillation, α,α,α-trifluoromethacrylic acid chloride (92.6 g) having a boiling point of from 88 to 92° C., was obtained (yield: 53%). Further, as a by-product, α,α,α-trifluoromethacrylic acid anhydride (34.0 g) having a boiling point of 106° C./31 mmHg was obtained (yield: 24%).

Into a 1,000 ml three-necked round-bottomed flask equipped with a dropping funnel and a stirrer, benzyl alcohol (54.6 g, 0.51 mol) and diethyl ether (600 ml) were charged, and then, the α,α,α-trifluoromethacrylic acid chloride (80.0 g, 0.51 mol) obtained as described above, was dropwise added at −40° C., and then a mixture comprising triethylamine (56.2 g, 0.56 mol) and diethyl ether (100 ml) was dropwise added. The mixture was stirred at −40° C. for one hour and then further stirred at 0° C. for one hour. To the reaction solution, a saturated ammonium chloride aqueous solution was added, and then, extracted with diethyl ether and dried over anhydrous magnesium sulfate, and the solvent was distilled off under reduced pressure. The residue was purified by silica gel column chromatography (hexane/ethyl acetate=9/1:vol/vol) to obtain α,α,α-trifluoromethacrylic acid benzyl ester (95.3 g) (yield: 82%).

Analytical Results
¹H-NMR(200 MHz,CDCl₃) δ 7.37–7.29(m, 5H), 6.70–6.67(m, 1H), 6.38–6.37(m, 1H), 5.25(s, 2H)

EXAMPLE 1

Preparation of (S)-2,3-epoxy-2-trifluoromethylpropionic acid benzyl ester

A 2,000 ml three-necked round-bottomed flask having a dropping funnel and a stirrer, was flushed with nitrogen, and then, molecular sieves 4A (46.3 g, product preliminarily dried under reduced pressure at 180° C. for 4 hours), (R)-1,1'-bi-2-naphthol (7.29 g, 25.5 mmol), triphenylphosphine oxide (19.3 g, 69.5 mmol) and THF (250 ml) were added. Stirring was carried out for 5 minutes for dissolution, and then a THF solution (250 ml) of lanthanum triisopropoxide (7.32 g, 23.2 mmol) was added, followed by stirring at room temperature for one hour. Cumene hydroperoxide (7.06 g, 46.4 mmol) was added, followed by further stirring at room temperature for two hours to prepare a catalyst.

After confirming that the reaction solution became green, the reaction solution was cooled to −20° C. Cumene hydroperoxide (89.8 g, 0.59 mol) was added, and then a THF (500 ml) solution of α,α,α-trifluoromethacrylic acid benzyl ester (106.6 g, 0.46 mol) was dropwise added over a period of one hour from the dropping funnel. After stirring at −20° C. for 12 hours, disappearance of the raw material was confirmed by ¹H-NMR.

A saturated ammonium chloride aqueous solution (300 ml) and a 5% sodium hydrogen sulfite aqueous solution (200 ml) were added to terminate the reaction, whereupon insoluble matters were filtered off by celite filtration, followed by liquid separation. The organic layer was concentrated and then, starting point components were removed by silica gel column chromatography (hexane/ethyl acetate=3/1:vol/vol). Further purification was carried out by silica gel column chromatography (hexane/ethyl acetate=9/1:vol/vol) to obtain (S)-2,3-epoxy-2-trifluoromethylpropionic acid benzyl ester (104.7 g) (yield: 92%, optical purity: 78 ee %).

Here, the measurement of the optical purity was carried out under the following conditions.

Column: CHIRALCEL OD-H (4.6 mmID×250 mm), manufactured by Daicel.

Eluent: hexane/isopropanol=9/1(vol/vol)

Flow rate: 1.0 ml/min

Detector: UV=254 nm

Retention time: 10.3 min (S), 11.2 min(R).

The (S)-2,3-epoxy-2-trifluoromethylpropionic acid benzyl ester obtained in Example 1 was isolated and purified by means of an optical resolution column (CHIRALCEL OD-H, manufactured by Daicel) and analyzed. The physical property values are shown below.

Analytical Results
¹H-NMR(200 MHz,CDCl₃) δ 7.48–7.26(m, 5H), 5.36–5.22(m, 2H), 3.27–3.19(m, 2H)

p ¹³C-NMR(50 MHz,CDCl₃) δ 163.40, 134.15, 128.74, 128.70, 128.19, 121.45(q, J=276.5 Hz), 68.30, 53.94(q, J=37.6 Hz), 49.02

IR (KBr: γ cm⁻¹) 3037, 2965, 1755, 1499, 1457, 1389, 1331, 1237, 1179, 1148, 1078, 1030, 958, 870, 782, 752, 696

Elemental analysis: C53.67; H3.68; F23.42 (Calc.: C53.64; H3.74; F23.15). MASS (m/z) 246 (M+) Specific rotation $(\alpha)_D^{25}$=9.8° (C=2.0, methanol)

EXAMPLE 2

Preparation of (R)-2,3-epoxy-2-trifluoromethylpropionic acid benzyl ester

The reaction was carried out in the same manner as in Example 1 by using (S)-1,1'-bi-2-naphthol instead of (R)-1,1'-bi-2-naphthol, to obtain (R)-2,3-epoxy-2-trifluoromethylpropionic acid benzyl ester (yield: 90%, optical purity: 78 ee %). ¹H and ¹³C-NMR and IR spectrum data were the same as shown in Example 1.

Analytical Results
Elemental analysis: C53.45; H3.78; F2,3.09 (Calc.: C53.64; H3.74; F23.15).

Specific rotation $(\alpha)_D^{25}$=9.8° (C=2.0, methanol)

EXAMPLE 3

Preparation of (S)-2,3-epoxy-2-trifluoromethylpropionic acid

Into a 500 ml three-necked round-bottomed flask equipped with a stirrer, (S)-2,3-epoxy-2- trifluoromethylpropionic acid benzyl ester (20.9 g, 84.9 mmol, 99 ee %) was charged, and 180 ml of methanol was added for dissolution. Platinum oxide (1.63 g) was added, and then, the reaction system was substituted by hydrogen. After stirring at room temperature for 4 hours, platinum oxide was filtered off. The solvent was distilled off under reduced pressure, whereupon (S)-2,3-epoxy-2-trifluoromethylpropionic acid (11.9 g) was obtained (yield: 90%).

Analytical Results $^1$H-NMR(CDCl$_3$) δ 9.28(br, 1H), 3.36–3.25(m, 2H)

$^{13}$C-NMR(CDCl$_3$) δ 168.76, 121.25(q, J=275.6 Hz), 53.71(q, J=38.5 Hz)

IR (KBr: γ cm$^{-1}$) 3528, 2928, 1744, 1636, 1388, 1318, 1259, 1179, 1090, 961, 875, 758, 684

Elemental analysis: C30.78; H1.94, F36.38 (Calc: C30.59, H1.80, F36.52)

MASS (m/z) 157 ((M+H)+)

Specific rotation $(α)_D^{25}$=10.9° (C=2.0, methanol)

EXAMPLE 4

Preparation of (R)-2,3-epoxy-2-trifluoromethylpropionic acid

The reaction was carried out under the same conditions as in Example 3 by using (R)-2,3-epoxy-2-trifluoromethylpropionic acid benzyl ester instead of (S)-2,3-epoxy-2-trifluoromethylpropionic acid benzyl ester, to obtain (R)-2,3-epoxy-2-trifluoromethylpropionic acid (yield: 93%). The $^1$H and $^{13}$C-NMR and IR spectrum data thereof were the same as shown in Example 3.

Analytical Results

Elemental analysis: C30.67, H1.72, F36.71 (Calc.: C30.59, H1.80, F36.52).

Specific rotation $(α)_D^{25}$=−10.9° (C=2.0, methanol)

EXAMPLE 5

Preparation of (S)--3,3,3-trifluoro-2-hydroxy-2-methylpropionic acid

Into a 500 ml three-necked round-bottomed flask equipped with a stirrer, a 1.0 M aluminum diisobutyl hydride/hexane solution (2400 ml, 2.40 mol) was charged in a nitrogen atmosphere. This solution was cooled to −80° C. A dichloromethane (600 g) solution of (S)-2,3-epoxy-2-trifluoromethylpropionic acid (149.82 g, 0.96 mol) was added over a period of two hours from a dropping funnel. After stirring at −70° C. for one hour, stirring was carried out at −50° C. for 6 hours. The reaction solution was cooled to −80° C., and a mixed solution of methanol (100 g) and dichloromethane (100 g) was dropwise added over a period of two hours to terminate the reaction. The reaction solution was dropwise added over a period of two hours to 1800 ml of a 18% HCl aqueous solution cooled to 0° C., and then, 160 g of sodium chloride was added. The mixture was extracted twice with 500 ml of diethyl ether, and the solvent was distilled off to obtain (S)-3,3,3-trifluoro-2-hydroxy-2-methylpropionic acid (98.6 g) (yield: 65%). This was recrystallized twice from toluene (400 ml) to obtain (S)-3,3,3-trifluoro-2-hydroxy-2-methylpropionic acid (51.6 g) having an optical purity of 99.9 ee % (yield: 34%). This product shows the same $^1$H and $^{13}$C-NMR and IR spectrum data as the already reported (S)-3,3,3-trifluoro-2-hydroxy-2-methylpropionic acid and therefore was determined to be (S)-3,3,3-trifluoro-2-hydroxy-2-methylpropionic acid.

Here, the measurement of the optical purity was carried out as follows. To the obtained crystals, an ether solution of diazomethane was added for methylesterification, and this solution was analyzed by gas chromatography (GC) under the following conditions, whereupon the optical purity was calculated.

Column: CP-Chiracil-Dex CB (0.25 mm×25 m), manufactured by Chrompak Company.

Column temperature: 70° C.

Detector: FID

Analytical Results

Specific rotation $(α)_D^{25}$=−18.9° (C=4.0, methanol)

EXAMPLE 6

Preparation of (R)-3,3,3-trifluoro-2-hydroxy-2-methylpropionic acid

The reaction was carried out under the same conditions as in Example 5 by using (R)-2,3-epoxy-2-trifluoromethylpropionic acid instead of (S)-2,3-epoxy-2-trifluoromethylpropionic acid, to obtain (R)-3,3,3-trifluoro-2-hydroxy-2-methylpropionic acid (yield: 36%). This product shows the same $^1$H and $^{13}$C-NMR and IR spectrum data as the already reported (R)-3,3,3-trifluoro-2-hydroxy-2-methylpropionic acid and therefore was determined to be (R)-3,3,3-trifluoro-2-hydroxy-2-methylpropionic acid.

Analytical Results

Specific rotation $(α)_D^{25}$=18.9° (C=4.0, methanol)

REFERENCE EXAMPLE 2

Preparation of α,α,α-trifluoromethacrylic acid phenyl ester

In the same manner as in Reference Example 1, α,α,α-trifluoromethacrylic acid phenyl ester (10.3 g, 47.7 mmol, yield: 63%) was obtained from α,α,α-trifluoromethacrylic acid chloride (10 g, 63.0 mmol), phenol (6.5 g, 69.0 mmol) and triethylamine (7.66 g, 75.7 mmol).

Analytical Results $^1$H-NMR (200 MHz, CDCl$_3$) δ 7.42–7.14 (m, 5H), 6.94–6.92 (m, 1H), 6.61–6.60 (m, 1H)

EXAMPLE 7

Preparation of (S)-2,3-epoxy-2-trifluoromethylpropionic acid phenyl ester

A 500 ml three-necked round-bottomed flask equipped with a dropping funnel and a stirrer was flushed with nitrogen, and then, molecular sieves 4A (3.7 g, product preliminarily dried under reduced pressure at 180° C. for 4 hours), (R)-1,1'-bi-2-naphthol (529.8 mg, 1.85 mmol), triphenylphosphine oxide (1.54 g, 5.6 mmol) and THF (90 ml) were added. Stirring was carried out for 5 minutes for dissolution, and then a THF solution (90 ml) of lanthanum triisopropoxide (585 mg, 1.85 mmol) was added, followed by stirring at room temperature for one hour. Cumene peroxide (740 μm, 80% pure product, 3.9 mmol) was added, followed by further stirring at room temperature for two hours to prepare a catalyst.

After confirming that the reaction solution became green, the reaction solution was cooled to −20° C. Cumene hydroperoxide (8.4 g, 80% pure product, 44.1 mmol) was added, and then, a THF (90 ml) solution of α,α,α-trifluoromethacrylic acid phenyl ester (8.0 g, 37.0 mmol)

was dropwise added over a period of one hour from a dropping funnel. After stirring at −20° C. for 12 hours, disappearance of the raw material was confirmed by $^1$H-NMR.

A saturated ammonium chloride aqueous solution (50 ml) and a 5% sodium hydrogen sulfite aqueous solution (10 ml) were added to terminate the reaction, and then, insoluble matters were filtered off by celite filtration, followed by liquid separation. The organic layer was concentrated, and then starting point components were removed by silica gel column chromatography (hexane/ethyl acetate=3/1:vol/vol). Further purification was carried out by silica gel column chromatography (hexane/ethyl acetate=9/1: vol/vol), to obtain (S)-2,3-epoxy-2-trifluoromethylpropionic acid phenyl ester (7.2 g, 31.0 mmol) (yield: 84%, optical purity: 79 ee %). Here, the measurement of the optical purity was carried out under the following conditions.

Analytical Results $^1$H-NMR(200 MHz, CDCl$_3$) δ 7.46–7.13(m, 5H), 3.46–3.41 (m, 1H), 3.36 (d, 1H, J=6.0 Hz)

$^{13}$C-NMR(500 MHz, CDCl$_3$) δ 162.17, 149.57, 129.35, 125.86, 121.42 (q, J=275.9 Hz), 120.84, 54.13(q, J=37.8 Hz), 49.33

IR (KBr: γ cm$^{-1}$) 3511, 3068, 1774, 1592, 1493, 1458, 1386, 1336, 1235, 1187, 1081, 1064, 1024, 1004, 959, 924, 877, 833, 747, 700, 687

Elemental analysis: C51.56; H3.18; F24.47 (Calc: C51.74, H3.04, F24.55).

MASS (m/z) 232 (M+)

Specific rotation $(α)_D^{25}$=0.9° (C=2.0, methanol)

EXAMPLE 8

Preparation of (S)-2,3-epoxy-2-trifluoromethylpropionic acid

Into a 100 ml three-necked round-bottomed flask equipped with a dropping funnel and a stirrer, the (S)-2,3-epoxy-2-trifluoromethylpropionic acid phenyl ester (7.2 g, 31.0 mmol) obtained in Example 7, methanol (20 ml) and water (20 ml) were charged and cooled to 0° C. on an ice bath, whereupon 3N sodium hydroxide aqueous solution (30 ml, 90 mmol) was dropwise added over a period of one hour by means of the dropping funnel, and stirring was further carried out at the same temperature for one hour. After completion of the reaction, methanol was distilled off, followed by extraction with diisopropyl ether (30 ml×twice). Then, hydrochloric acid was added to adjust the pH to 3, followed by extraction with ethyl acetate (30 ml×3 times). The obtained organic layer was dried over anhydrous magnesium sulfate, followed by filtration and concentration to obtain the desired (S)-2,3-epoxy-2-trifluoromethylpropionic acid (4.17 g, 26.7 mmol, yield: 87%, optical purity: 78% ee).

REFERENCE EXAMPLE 3

Preparation of α,α,α-trifluoromethacrylic acid (p-chloroanilide)

In the same manner as in Reference Example 1,α,α,α-trifluoromethacrylic acid (m-chloroanilide) (14.5 g, 58.0 mmol, yield: 92%) was obtained from α,α,α-trifluoromethacrylic acid chloride (10 g, 63.0 mmol), m-chloroaniline (8.9 g, 69.4 mmol) and triethylamine (7.00 g, 69.4 mmol).

Analytical Results $^1$H-NMR (200 MHz, CDCl$_3$) δ 7.68–7.13 (m, 4H), 6.68–6.65 (m, 1H), 6.38–6.37 (m, 1H)

EXAMPLE 9

Preparation of (S)-2,3-epoxy-2-trifluoromethylpropionic acid (m-chloroanilide)

A 1,000 ml three-necked round-bottomed flask equipped with a dropping funnel and a stirrer was flushed with nitrogen, and then, molecular sieves 4A (3.70 g, product preliminarily dried under reduced pressure at 180° C. for 4 hours), (R)-1,1'-bi-2-naphthol (2.11 g, 7.37 mmol), triphenylphosphine oxide (6.15 g, 22.1 mmol) and THF (100 ml) were added. Stirring was carried out for 5 minutes for dissolution, and then, a THF solution (100 ml) of lanthanum triisopropoxide (2.33 g, 7.37 mmol) was added, followed by stirring at room temperature for one hour. Cumene hydroperoxide (2.80 g, 80% pure product, 14.7 mmol) was added, followed by further stirring at room temperature for two hours, to prepare a catalyst.

After confirming that the reaction solution became green, the reaction solution was cooled to −20° C. Cumene hydroperoxide (6.31 g, 80% pure product, 33.16 mol) was added, and then a THF (100 ml) solution of α,α,α-trifluoromethacrylic acid (m-chloroanilide) (9.20 g, 36.8 mmol) was dropwise added over a period of one hour from the dropping funnel. After stirring at −20° C. for 12 hours, disappearance of the raw material was confirmed by $^1$H-NMR.

A saturated ammonium chloride aqueous solution (200 ml) and a 5% sodium hydrogen sulfite aqueous solution (150 ml) were added to terminate the reaction, whereupon insoluble matters were filtered off by celite filtration, followed by liquid separation. The organic layer was concentrated and then, starting point components were removed by silica gel column chromatography (hexane/ethyl acetate=3/1:vol/vol). Further purification was carried out by silica gel column chromatography (hexane/ethyl acetate=9/1:vol/vol), to obtain (S)-2,3-epoxy-2-trifluoromethylpropionic acid (m-chloroanilide) (7.54 g, 28.5 mmol) (yield: 77%, optical purity: 84 ee %).

Analytical Results $^1$H-NMR(200 MHz, CDCl$_3$) δ 7.68–7.10(m, 4H), 4.12 (d, 1H, J=4.4 Hz), 3.19 (d, 1H, J=4.4 Hz)

Elemental analysis: C54.12, H2.87, N5.19, Cl13.19, F21.35 (Calc: C45.22, H2.66, N5.27, Cl13.35, F21.46).

MASS (m/z) 265 (M+)

Specific rotation $(α)_D^{25}$=7.3° (C=2.0, methanol)

EXAMPLE 10

Preparation of (S)-2,3-epoxy-2-trifluoromethylpropionic acid

Into a 300 ml round-bottomed flask equipped with a stirrer, the (S)-2,3-epoxy-2-trifluoromethylpropionic acid (m-chloroanilide) (7.54 g, 28.5 mmol) obtained in Example 9, methanol (100 ml) and 35% hydrochloric acid (25 ml) were charged and stirred at room temperature for 4 days.

After completion of the reaction, methanol was distilled off, followed by extraction with ethyl acetate (30 ml×three times). The obtained organic layers were put together and washed with 1N hydrochloric acid (20 ml×twice), followed by drying over anhydrous magnesium sulfate, filtration and concentration to obtain the desired (S)-2,3-epoxy-2-trifluoromethylpropionic acid (2.75 g, 17.6 mmol, yield: 62%, optical purity: 84% ee).

The entire disclosure of Japanese Patent Application No. 2002-340758 filed on Nov. 25, 2002 including specification, claims and summary is incorporated herein by reference in its entirety.

What is claimed is:

1. An optically active fluorine-containing compound represented by the following formula (1):

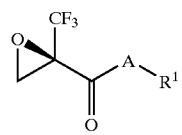

wherein A is an oxygen atom, a sulfur atom or an NH group, and $R^1$ is a methyl group, an ethyl group, a $C_{3-10}$ linear, branched or cyclic alkyl group, a $C_{6-20}$ aromatic group, a $C_{6-20}$ aromatic group having hydrogen on the aromatic ring optionally substituted by a halogen atom, a $C_{6-20}$ aromatic group having hydrogen on the aromatic ring optionally substituted by a methyl group, a $C_{6-20}$ aromatic group having hydrogen on the aromatic ring optionally substituted by an ethyl group, a $C_{6-20}$ aromatic group having hydrogen on the aromatic ring optionally substituted by a $C_{3-6}$ linear, branched or cyclic alkyl group, a $C_{6-20}$ aromatic group having hydrogen on the aromatic ring optionally substituted by a methoxy group, a $C_{6-20}$ aromatic group having hydrogen on the aromatic ring optionally substituted by an ethoxy group, a $C_{6-20}$ aromatic group having hydrogen on the aromatic ring optionally substituted by a $C_{3-6}$ linear, branched or cyclic alkyloxy group, a $C_{5-19}$ heteroaromatic group, a $C_{5-19}$ heteroaromatic group having hydrogen on the aromatic ring optionally substituted by a halogen atom, a $C_{5-19}$ heteroaromatic group having hydrogen on the aromatic ring optionally substituted by a methyl group, a $C_{5-19}$ heteroaromatic group having hydrogen on the aromatic ring optionally substituted by an ethyl group, a $C_{5-19}$ heteroaromatic group having hydrogen on the aromatic ring optionally substituted by a $C_{3-6}$ linear, branched or cyclic alkyl group, a $C_{5-19}$ heteroaromatic group having hydrogen on the aromatic ring optionally substituted by a methoxy group, a $C_{5-19}$ heteroaromatic group having hydrogen on the aromatic ring optionally substituted by an ethoxy group, a $C_{5-19}$ heteroaromatic group having hydrogen on the aromatic ring optionally substituted by a $C_{3-6}$ linear, branched or cyclic alkyloxy group, a benzyl group, a benzyl group having hydrogen on the aromatic ring optionally substituted by a halogen atom, a benzyl group having hydrogen on the aromatic ring optionally substituted by a methyl group, a benzyl group having hydrogen on the aromatic ring optionally substituted by an ethyl group, a benzyl group having hydrogen on the aromatic ring optionally substituted by a $C_{3-6}$ linear, branched or cyclic alkyl group, a 2-phenylethyl group, or a $C_{3-10}$ linear, branched or cyclic alkyl group having a $C_{6-20}$ aromatic group bonded thereto, or by the following formula (2):

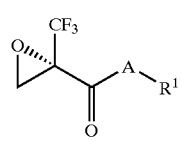

wherein A and $R^1$ are as defined above.

2. The optically active fluorine-containing compound according to claim 1, wherein in the formula (1) or (2), A is an oxygen atom or NH group, and $R^1$ is a tert-butyl group, a phenyl group, a phenyl group having hydrogen on the aromatic ring substituted by a halogen atom, or a benzyl group.

3. An optically active fluorine-containing compound represented by the following formula (3) or (4):

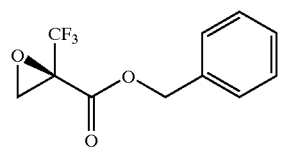

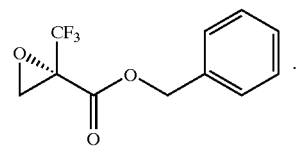

4. A process for producing an optically active fluorine-containing compound as defined in claim 1, which comprises asymmetrically epoxidizing an α,α,α-trifluoromethacrylic acid derivative represented by the following formula (5):

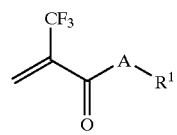

wherein A is an oxygen atom, a sulfur atom or an NH group, and $R^1$ is a methyl group, an ethyl group, a $C_{3-10}$ linear, branched or cyclic alkyl group, a $C_{6-20}$ aromatic group, a $C_{6-20}$ aromatic group having hydrogen on the aromatic ring optionally substituted by a halogen atom, a $C_{6-20}$ aromatic group having hydrogen on the aromatic ring optionally substituted by a methyl group, a $C_{6-20}$ aromatic group having hydrogen on the aromatic ring optionally substituted by an ethyl group, a $C_{6-20}$ aromatic group having hydrogen on the aromatic ring optionally substituted by a $C_{3-6}$ linear, branched or cyclic alkyl group, a $C_{6-20}$ aromatic group having hydrogen on the aromatic ring optionally substituted by a methoxy group, a $C_{6-20}$ aromatic group having hydrogen on the aromatic ring optionally substituted by an ethoxy group, a $C_{6-20}$ aromatic group having hydrogen on the aromatic ring optionally substituted by a $C_{3-6}$ linear, branched or cyclic alkyloxy group, a $C_{5-19}$ heteroaromatic group, a $C_{5-19}$ heteroaromatic group having hydrogen on the aromatic ring optionally substituted by a halogen atom, a $C_{5-19}$ heteroaromatic group having hydrogen on the aromatic ring optionally substituted by a methyl group, a $C_{5-19}$ heteroaromatic group having hydrogen on the aromatic ring optionally substituted by an ethyl group, a $C_{5-19}$ heteroaromatic group having hydrogen on the aromatic ring optionally substituted by a $C_{3-6}$ linear, branched or cyclic alkyl group, a $C_{5-19}$ heteroaromatic group having hydrogen on the aromatic ring optionally substituted by a methoxy group, a $C_{5-19}$ heteroaromatic group having hydrogen on the aromatic ring optionally substituted by an ethoxy group, a $C_{5-19}$ heteroaromatic group having hydrogen on the aromatic ring optionally substituted by a $C_{3-6}$ linear, branched or cyclic alkyloxy group, a benzyl group, a benzyl group having hydrogen on the aromatic ring optionally substituted by a halogen atom, a benzyl group having hydrogen on the aromatic ring optionally substituted by a methyl group, a benzyl group having hydrogen on the aromatic ring optionally substituted by an ethyl group, a benzyl group having hydrogen on the aromatic ring optionally substituted by a $C_{3-6}$ linear, branched or cyclic alkyl group, a 2-phenylethyl group, or a $C_{3-10}$ linear, branched or cyclic alkyl group having a $C_{6-20}$ aromatic group bonded thereto.

5. The process for producing an optically active fluorine-containing compound according to claim 4, wherein in the formula (5), A is an oxygen atom, and $R^1$ is a tert-butyl group, a phenyl group, a phenyl group having hydrogen on the aromatic ring substituted by a halogen atom, or a benzyl group.

6. The process for producing an optically active fluorine-containing compound according to claim 4, wherein in the formula (5), A is an oxygen atom, and $R^1$ is a benzyl group.

7. The process for producing an optically active fluorine-containing compound according to claim 4, wherein the α,α,α-trifluoromethacrylic acid derivative represented by the formula (5) is subjected to the asymmetric epoxidizing reaction in the presence of a catalyst comprising (A) a rare earth metal alkoxide, (B) optically active 1,1'-bi-2-naphthol, (C) triphenylphosphine oxide and (D) cumene hydroperoxide or tert-butyl hydroperoxide.

8. The process for producing an optically active fluorine-containing compound according to claim 7, wherein (A) the rare earth metal alkoxide is a lanthanoid triisopropoxide.

9. The process for producing an optically active fluorine-containing compound according to claim 7, wherein (A) the rare earth metal alkoxide is lanthanum triisopropoxide.

10. An optically active fluorine-containing compound represented by the following formula (6) or (7):

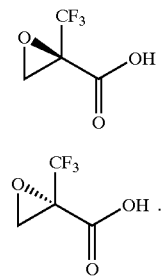

(6)

(7)

11. A process for producing the optically active fluorine-containing compound represented by the formula (6):

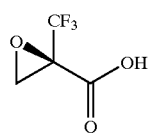

(6)

which comprises hydrolyzing the optically active fluorine-containing compound represented by the formula (1) in claim 1.

12. A process for producing the optically active fluorine-containing compound represented by the formula (7):

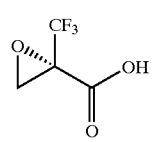

(7)

which comprises hydrolyzing the optically active fluorine-containing compound represented by the formula (2) in claim 1.

13. A process for producing the optically active fluorine-containing compound represented by the formula (6):

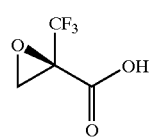

(6)

which comprises hydrolyzing or hydrogenating the optically active fluorine-containing compound represented by the formula (3) in claim 3.

14. A process for producing the optically active fluorine-containing compound represented by the formula (7):

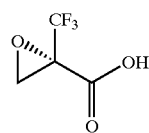

(7)

which comprises hydrolyzing or hydrogenating an optically active fluorine-containing compound represented by the formula (4) in claim 3.

15. A process for producing (R)-3,3,3-trifluoro-2-hydroxy-2-methylpropionic acid, which comprises reacting the optically active fluorine-containing compound represented by the formula (6) in claim 10, with a metal hydride.

16. A process for producing (S)-3,3,3-trifluoro-2-hydroxy-2-methylpropionic acid, which comprises reacting the optically active fluorine-containing compound represented by the formula (7) in claim 10, with a metal hydride.

* * * * *

UNITED STATES PATENT AND TRADEMARK OFFICE
CERTIFICATE OF CORRECTION

PATENT NO. : 6,921,832 B2
DATED : July 26, 2005
INVENTOR(S) : Miyata et al.

It is certified that error appears in the above-identified patent and that said Letters Patent is hereby corrected as shown below:

Title page,
Item [12], delete "Miyama et al" and insert -- Miyata et al --.
Item [75], Inventors, delete and insert:
-- Takuya Miyata, Yamaguchi-ken (JP);
Toshio Naka, Yamaguchi-ken (JP);
Takumi Kagawa, Yamaguchi-ken (JP) --.

Signed and Sealed this

Twentieth Day of September, 2005

JON W. DUDAS
*Director of the United States Patent and Trademark Office*